United States Patent [19]

Schoenbaum et al.

[11] Patent Number: 4,695,157

[45] Date of Patent: Sep. 22, 1987

[54] SOLDER PROCESS INSPECTION DIFFUSER ASSEMBLY

[75] Inventors: Gary L. Schoenbaum, Newtown; Lewis A. Latanzi, Roxbury; Stephen L. Hedrick; Harold V. Johnson, both of Danbury, all of Conn.

[73] Assignee: Benchmark Industries Incorporated, Manchester, N.H.

[21] Appl. No.: 786,609

[22] Filed: Oct. 11, 1985

[51] Int. Cl.⁴ .............................................. G01N 21/47
[52] U.S. Cl. ..................................... 356/237; 356/446; 250/563
[58] Field of Search ......................... 356/237, 349, 446; 250/492.2, 563; 350/276 R

[56] References Cited

U.S. PATENT DOCUMENTS

| | | | |
|---|---|---|---|
| 1,890,828 | 12/1932 | Richardson et al. | 350/117 |
| 2,364,369 | 12/1944 | Jelley et al. | 350/117 |
| 2,368,099 | 1/1945 | Bodde | 350/117 |
| 2,383,493 | 8/1945 | Mercer | 350/117 |
| 3,170,068 | 2/1965 | Petriw et al. | 356/230 |
| 3,264,769 | 8/1966 | Hardesty | 362/351 |
| 3,300,646 | 1/1967 | Casebeer | 350/431 |
| 3,349,665 | 3/1967 | Grosheim | 356/236 |
| 3,461,295 | 8/1969 | Camack | 250/492.1 |
| 3,479,501 | 2/1969 | Pisciotta et al. | 362/355 |
| 3,545,871 | 12/1970 | Waska | 356/236 |
| 3,561,842 | 4/1971 | Horton | 350/431 |
| 3,637,285 | 1/1972 | Stewart | 350/431 |
| 3,711,701 | 1/1973 | Squyres | 356/236 |
| 3,713,741 | 1/1973 | Sheehan | 356/237 |
| 3,720,827 | 3/1973 | Hemphill | 350/431 |
| 3,737,226 | 6/1973 | Shank | 355/67 |
| 3,807,868 | 4/1974 | Simila | 356/118 |
| 4,028,728 | 6/1977 | Sharp | 358/106 |
| 4,076,426 | 2/1978 | Gross | 356/239 |
| 4,083,626 | 4/1978 | Miyahara | 350/117 |
| 4,111,561 | 9/1978 | Plummer | 350/431 |
| 4,184,175 | 1/1980 | Mullane, Jr. | 358/93 |
| 4,378,159 | 3/1983 | Galbraith | 356/237 |

FOREIGN PATENT DOCUMENTS 0219441  12/1983  Japan ................................. 356/237

*Primary Examiner*—Eugene R. LaRoche
*Assistant Examiner*—Robert J. Pascal
*Attorney, Agent, or Firm*—Mattern, Ware, Stoltz & Fressola

[57] ABSTRACT

An optical unit for inspecting the soldered surface of a printed circuit board incorporates a thick-walled translucent concave diffuser dome with a hollow central cavity facing the surface under inspection, lamps directing illumination on the exterior of the dome, inspection portals spaced around the diffuser dome for video camera inspection of the board surface, and X-Y maneuvering control means governing the relative scanning repositioning of the board surface and the dome. A light baffle between each camera and its inspection portal, incorporating alternately white and black conically chamfered rings, produces improved imaging of the inspected surface, and a flexible translucent skirt extending from the dome rim to the inspected surface, preferably formed of a large plurality of white plastic bristles, blocks direct illumination and assures substantially uniform diffused illumination of the inspected surface.

12 Claims, 4 Drawing Figures

SOLDER PROCESS INSPECTION DIFFUSER ASSEMBLY

This invention relates to inspection units for video scanning inspection of soldered connections on printed circuit boards, and particularly to light diffusers for illuminating the circuit board by means of a diffused field of illumination, eliminating bright spots or specular reflections in the video images, and employing light baffles to eliminate dark spot images of video camera lenses by minimizing the apparent size of the image of the lens reflected in the smooth shiny surfaces of the fresh solder connections.

Prior art techniques for locating and identifying faults or voids in solder connections on printed circuit boards include such proposals as the Western Electric Company's Sheehan U.S. Pat. No. 3,713,741, employing color filters to highlight solder segments differing from those intended, and the Western Electric Company's Sharp U.S. Pat. 4,028,728 employing a video camera and a circular illumination source with rotatable polarizing filters. These devices, as well as visual inspection by human inspectors, may fail to identify solder flaws or gaps because of errors introduced by the smooth, shiny, highly reflective surfaces of fresh solder. Bright illumination sources such as incandescent filaments and dark objects such as the lens of the inspection video camera may both provide error sources, reducing the precision of the inspection techniques.

The solder inspection units of the present invention overcome these disadvantages by producing highly diffused illumination, substantially uniform over the entire region surrounding the printed circuit board solder connections under inspection, substantially eliminating filament images or bright spots which might be reflected in smooth, fresh solder surfaces and thereby imaged by inspection video cameras.

This objective is achieved by a thick translucent diffuser dome formed in the shape of a hemisphere whose outer surface is illuminated by such means as spotlights beamed directly upon it. Attenuation and light dispersion within the internal structure of the thick translucent dome material cooperate to produce less bright and substantially uniform diffuse illumination over its entire interior surface.

A small plurality of observation portals formed in the dome permit aligned video cameras to observe the space near the center of the dome, where the solder joints joining components with cladding on the printed circuit board to be inspected are positioned and maneuvered during the examination.

A unique light baffle with alternating light and dark chamfered rings inside a baffle housing is employed to minimize the size of the virtual image of each inspection portal lens and to enhance the contrast of the region surrounding the virtual image reflected in the smooth surfaces of the solder under inspection.

Accordingly, a principal object of the present invention is to provide automatic optical inspection of the soldered joints of loaded printed circuit boards. The device successfully monitors soldering processes which achieve high production rates of printed circuit boards for industrial and commercial products.

Another object of the invention is to provide such printed circuit board inspection systems and apparatus taking advantage of a unique light diffusion dome of thick translucent material receiving illumination on its exterior surface and producing substantially uniform and diffuse lower intensity illumination throughout its interior, with which the printed circuit board under inspection is juxtaposed.

A further object of the invention is to enhance the substantially uniform diffusion of illumination in the interior of the diffusion dome in such inspection systems by employing a flexible rim or skirt of translucent material bridging the gap between the dome's rim and the juxtaposed printed circuit board.

Still another object of the invention is to provide such printed circuit board inspection systems and apparatus taking advantage of minimized virtual images of video camera lenses reflected in smooth, fresh soldered surfaces by employing a stacked light baffle of a plurality of alternating light and dark colored chamfered rings encircling the optical axis of each inspection video camera.

A still further object of the invention is to provide automated solder process inspection systems and apparatus capable of being employed with suitable software to enhance the inspection images, to flag defective boards and to compile statistical reports and information for the user, and to be connected by communication links to host computers.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

For a fuller understanding of the nature and objects of the invention, reference should be had to the following detailed description taken in connection with the accompanying drawings, in which:

THE DRAWINGS

BEST MODE FOR CARRYING OUT THE INVENTION

Figure 1:
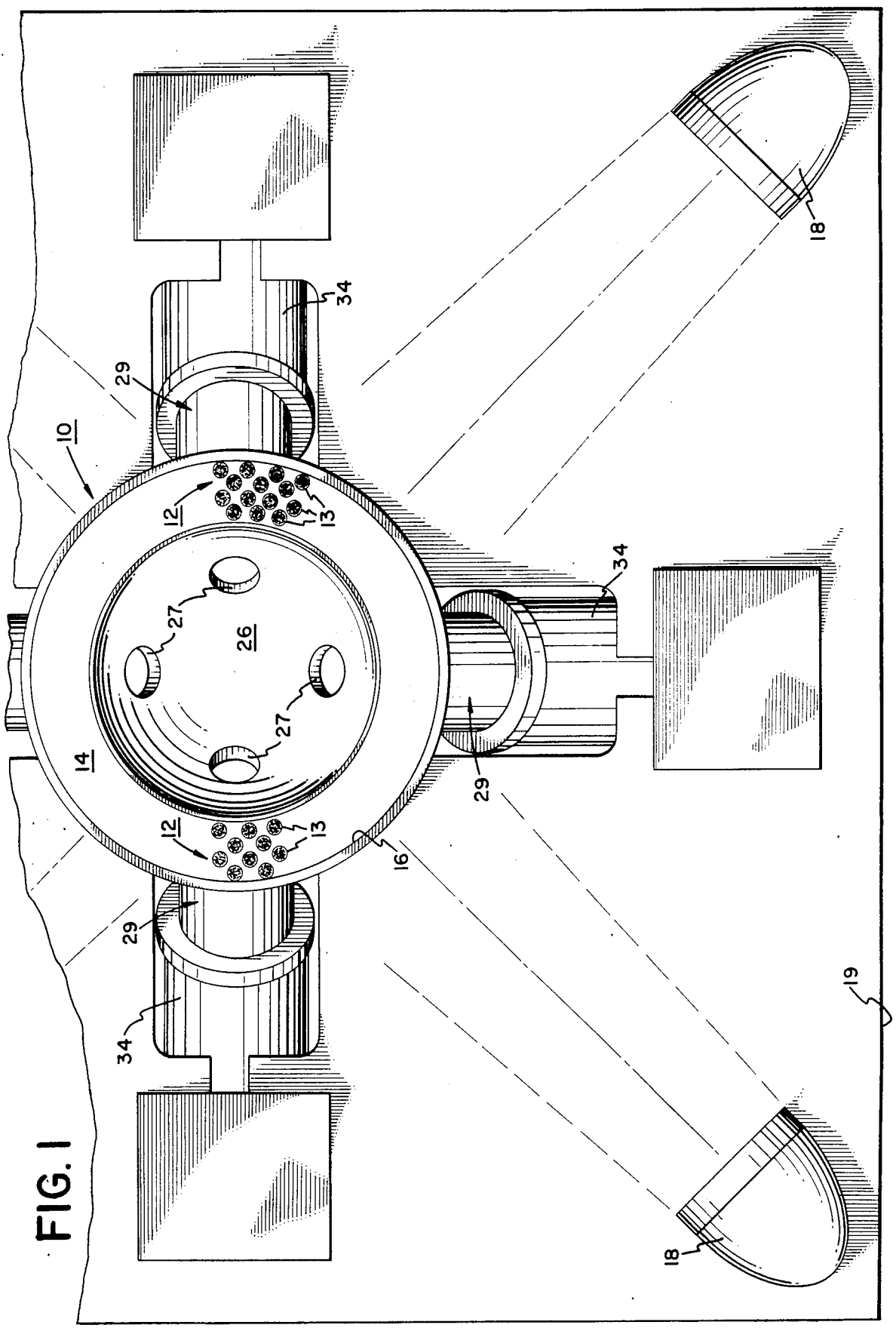
FIG. 1 is a fragmentary top plan view of the light diffuser and video camera inspection unit mounted at the soldered printed circuit board inspection station in the devices of the present invention.
Figure 2:
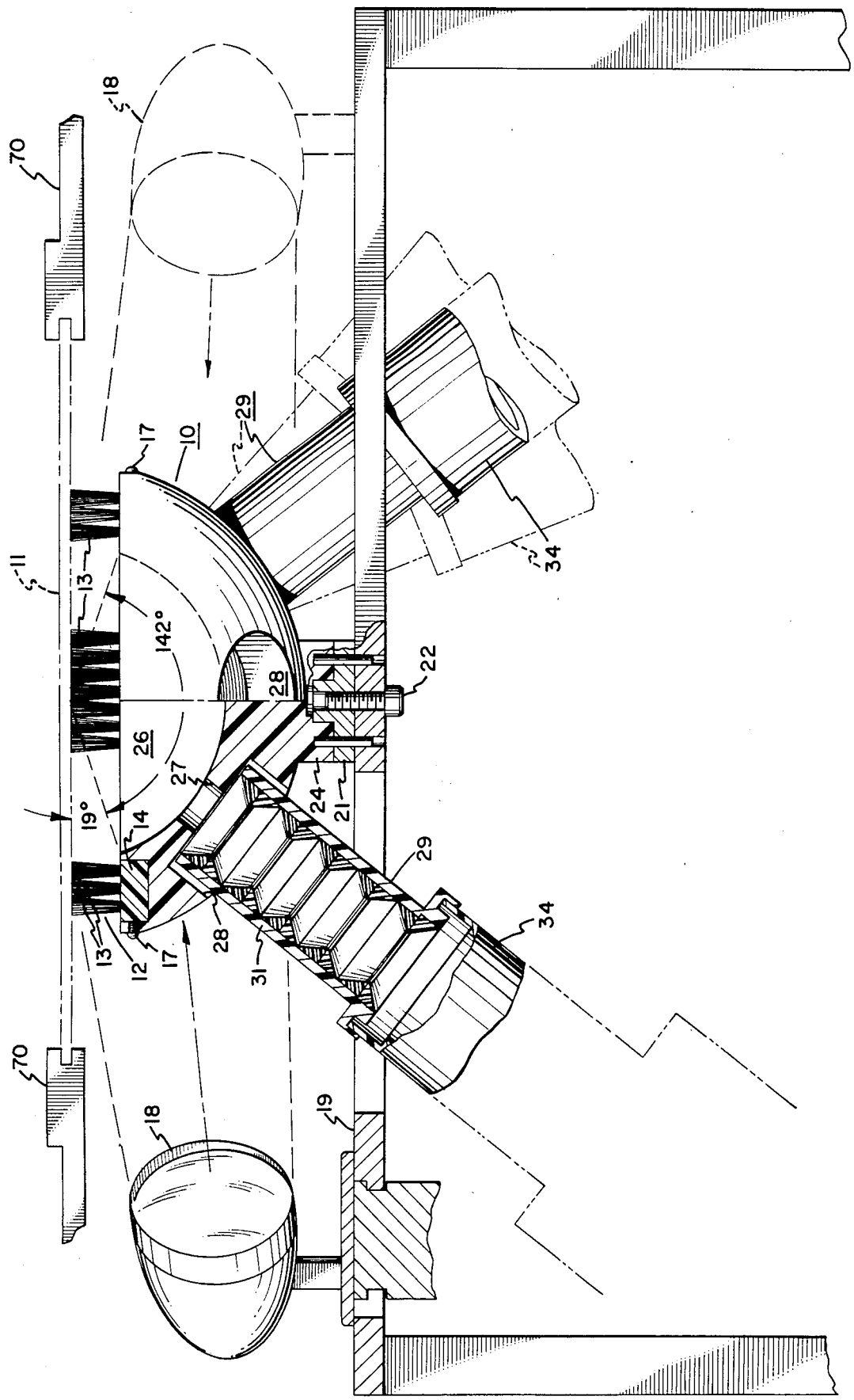
FIG. 2 is a front elevation view partially in cross-section of the same light diffuser and video camera inspection station, broken away to show its internal construction.

The video camera printed circuit board inspection station illustrated in FIGS. 1 and 2 incorporates a unique form of externally illuminated, translucent light diffuser dome generally indicated at 10 in the FIGURES. This diffuser dome may take the form of a cylindrical or conical or box-shaped semi-enclosure, with a concave interior region facing outward, with which a printed circuit board may be juxtaposed with its soldered surface closing the open face of the concave dome enclosure. The preferred form of the diffuser dome 10 illustrated in the FIGURES is a spherical sector. This sector subtends an included angle, measured from its interior rim edge to the sphere's center, coinciding with the central portion of the juxtaposed printed circuit board 11 shown in dot-dash lines. In FIG. 2, this angle is shown to be about 142 degrees, leaving a 19-degree ring-shaped sector encircling and extending from the rim of the dome to the board 11, which is spanned by a resilient flexible translucent light screen structure 12.

In the preferred form of the invention, the light screen 12 is formed by a large plurality of translucent bristles 13 of nylon or similar material, whose mounting ends are embedded in a mounting ring 14 recessed in a mating rim groove 16 formed in the open rim of dome 10. Mounting ring 14 is secured in rim groove 16 by one or more set screws 17, with bristles 13 protruding from the rim and preferably extending from the dome 10 toward and into close proximity or contact with printed circuit board 11. Bristles 13 form a translucent light barrier 12, preventing direct external illumination from penetrating between diffuser dome 10 and printed circuit board 11. Bristles 13 preferably engage the surface of board 11 with flexing contact, easily straddling protruding connector pins, conductor wires, components, or other irregularities on the board surface under inspection.

As indicated in the drawings, dome 10 is preferably formed of a thick body of translucent plastic material, preferably white polyethylene, and mounting ring 14 may be formed of the same material. Bristles 13 are also preferably formed of translucent white material A plurality of directed illumination sources, such as incandescent spotlights 18, are mounted near the corners of a rectangular mounting plate 19, aimed at the exterior of dome 10. Dome 10 is mounted by a pedestal 21 at the central portion of mounting plate 19, anchored by a sturdy mounting screw 22 and alignment pins 23 extending from suitable alignment holes in plate 19 and pedestal 21 into aligned apertures in a boss 24 integrally molded or machined on the external surface of dome 10.

The thick translucent body of dome 10 and the similar translucent ring 14, and the translucent bristles 13 forming rim screen 12, all cooperate to form a light diffuser totally isolating the facing surface of circuit board 11 from all external illumination. The light energy delivered by lights 18 to the outer surfaces of dome 10 and of the bristle rim screen 12-13 is significantly attenuated by internal absorption, with the result that the concave interior cavity 26 on the inside of dome 10 facing printed circuit board 11 is illuminated by a substantially uniform diffused level of illumination which eliminates shadows and bright spots, thereby maximizing the precision of the video camera images of the soldered joints of each printed circuit board 11 presented to interior cavity 26 for observation.

Television viewers are familiar with the images of headlights, spotlights, torches and other bright light sources delivered to the video screen producing "overload" flares or slashes reminiscent of the persistence of vision images delivered by the human eye to the brain when the viewer makes a scanning glance at the sun or a bright light source. All such "overload" images are eliminated by the substantially diffuse illumination produced inside the dome of the present invention. This is true whether the dome is hemispherical in shape, as in the preferred form shown in the drawings, or takes other shapes, such as square or rectangular box shapes, cylinders, cones or polyhedral domes, provided these diffuser domes are relatively thick, on the order of two to three centimeters in radial thickness, with a comparable radial thickness of rim screen bristles 12 blocking direct illumination between the dome rim and the juxtaposed printed circuit board.

In the preferred form of the invention shown in the drawings, four video camera viewing portals 27 are formed in the spherical sector diffusion dome 10 at 90 degree increments of longitude around the dome and at central positions generally corresponding to south latitudes between 50 and 55 degrees south. The dome 10 thus may be viewed as an analogue of the southern hemisphere of the spherical earth, with the Mercator parallels of latitude and meridians of longitude inscribed thereon, and with its upper rim defined by mounting ring 14 corresponding to the point on the interior of dome 10 which is approximately equated to the parallel of 19 degrees south latitude. In this analogy, mounting screw 22 stands at the south pole, and the soldered surface of board 11 preferably spans the equatorial plane.

Figure 4:
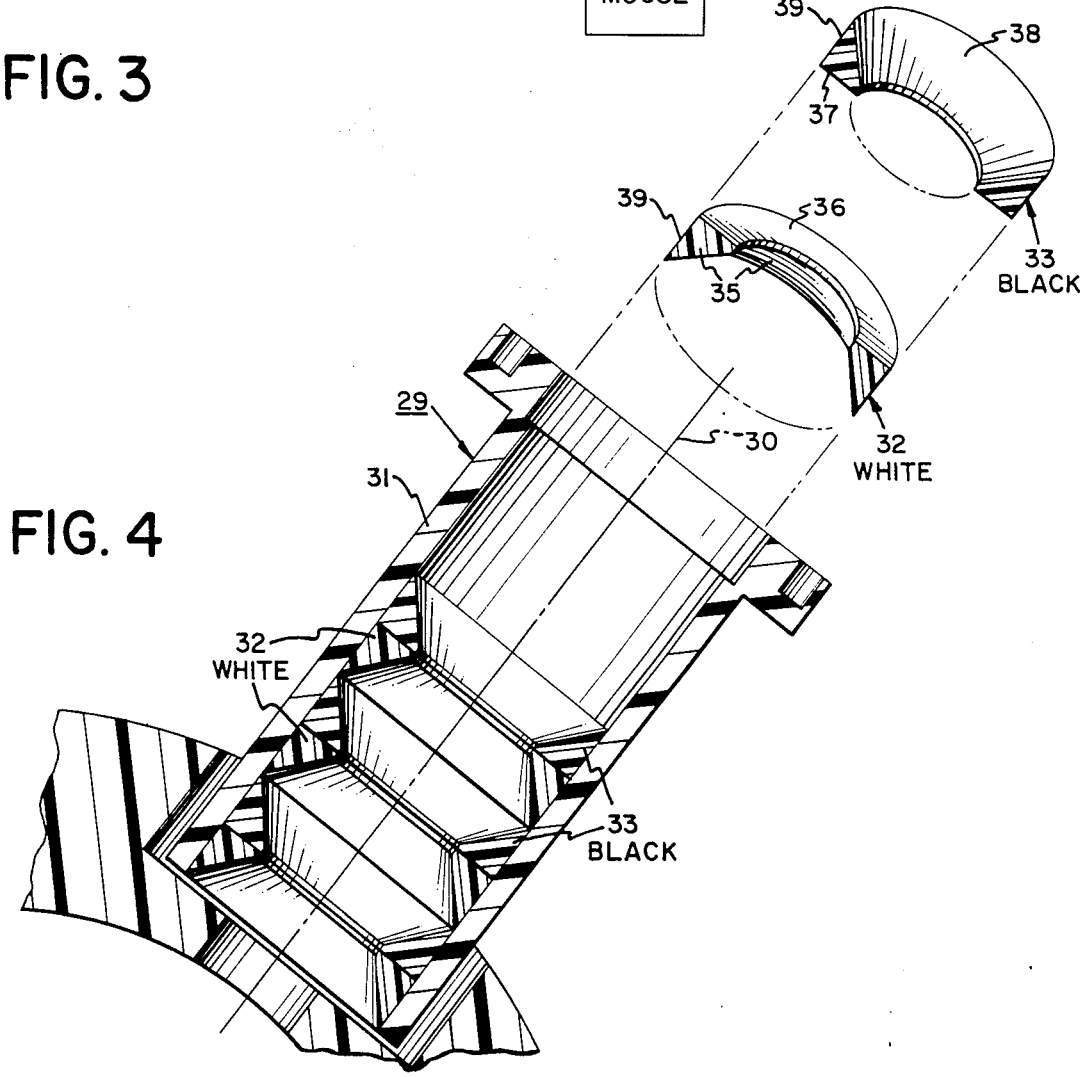
FIG. 4 is an enlarged fragmentary cross-sectional side elevation view of the inspection portal baffle assembly showing its various chamfered ring components.

Each portal 27 is provided with an enlarged exterior baffle recess 28, as shown in FIGS. 2 and 4, each loosely embracing the viewing end of a light baffle assembly 29. The preferred form of assembly 29 illustrated in FIGS. 2 and 4 comprises a hollow translucent polymer tube 31 embracing an arrayed series of pairs of alternatingly conically-chamfered polymer rings, rings 32 having their slanting conical chamfered surfaces 35 facing inward toward axis 30 of the portal 27 and the interior cavity 26 of dome 10, and rings 33 having their slanting conical chamfered surfaces 38 facing outward toward the video camera 34 viewing the interior 26 of the dome. Rings 32 have radial walls 36 each facing an adjacent radial wall 37 of the adjoining ring 33. Rings 32 and 33 each have an outer peripheral wall 39 facing the inside wall of baffle tube 31. It will be noted in FIG. 4 that the inward facing rings 32 which may be observed fragmentarily from the interior of the dome looking through portal 27 are preferably of white translucent polymer material, while the outward facing rings 33 which can be viewed only by the video camera are preferably formed of black opaque polymer material.

By this means, internal reflections of illumination from the interior cavity 26 of dome 10 entering the tubular baffle assembly 29 and stray light entering through translucent tube 31 will be largely absorbed by the black rings 33 of each pair of rings 32-33, and only the small central region of each of the white outward facing rings 32 may be viewed through portal 27. This makes the apparent or virtual size of the video camera lens viewed through portal 27 to appear to have the smallest possible diameter, and reduces the apparent size of its reflected virtual image in each smooth solder surface.

As indicated in the figures, the rings 32 and 33 alternating in arrayed relationship, successively positioned inside tube 31, form three or four pairs of successive white and black rings achieving maximum effect in a convenient and highly economical manner.

The dash lines shown in FIG. 2 illustrate the adjustability of the baffle assembly 29 and its associated camera 34 which may be rocked through significant angles relative to baffle recess 28, to provide the precise desired view of the central portion of board 11 exposed through portal 27 and the interior cavity 26 in dome 10.

Figure 3:
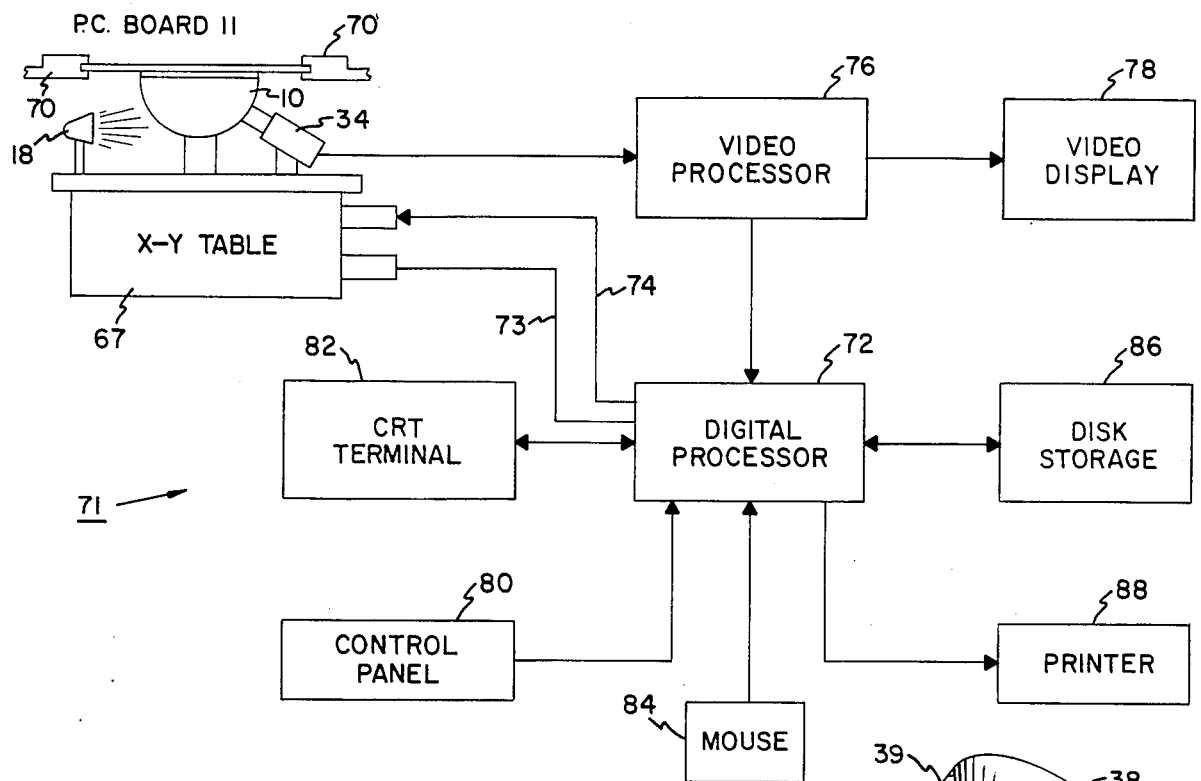
FIG. 3 is a schematic circuit diagram of the computer control system connected to the inspection station and video camera units in the system of this invention.

The control circuitry 71 governing overall operation, including both movement and inspection of printed circuit board 11, is best seen in FIG. 3. The printed circuit board 11 is mounted to an external frame 70 so as to be fixed near plate 19 on which dome 10 is mounted. It is readily seen that by movement of plate 19 in a plane parallel to that of printed circuit board 11, the dome 10 can be moved relative to the printed circuit board thereby allowing inspection of the entire surface area of the printed circuit board. Indeed plate 19 is preferably mounted on a standard X-Y table 69, allowing movement along two coordinate axes under the control of information received via digital processor 72 forming part of control electronics 71 shown schematically in FIG. 3. While movement of plate 19 relative to board 11 is illustrated, movement of board 11 and its supporting frame 70 relative to table 19 may be utilized instead, if desired. Output signals 73 and 74 from the digital processor provide the necessary information to the X-Y table 69 in order to position dome 10 for scanning past the entire surface of circuit board 11.

In order to achieve this movement of the X-Y table, information from the video cameras 34 is presented to the video processor 76, where it is in turn transferred to a video display 78 and to the digital processor 72. The video display provides the means for operator review of the inspection process, while the program information transferred from digital processor 72 provides the input information necessary to move X-Y table 69 in the two Cartesian coordinates and thereby provide for inspection of the entire printed circuit board.

The digital processor 72, in addition to driving output 73 and 74, provides for the actual inspection of the printed circuit board so as to detect such conditions as the lack of solder, solder voids, and solder bridges between traces on the printed circuit board. It also generates an alarm if a high fault rate condition is detected and provides information regarding defects including statistical reports, trend information and the flagging of defects.

In the preferred embodiment of the present invention, the digital processor 72 can inspect the printed circuit board at the rate of one square inch of board area in three seconds, with the maximum board area inspectable at any one time normally being about 18 inches (45.72 centimeters) ×18 inches (45.72 centimenters).

As also seen in FIG. 3, the control circuitry further includes a control panel 80 for operator input of instructions and other information to the digital processor, a CRT terminal 82 for interrogating the digital processor as well as inputting of certain commands to the digital processor, a mouse 84 for the input of coordinate movement information, as well as a disk storage unit 86 for the storage of program and data and a printer 88 for the printing of various test results.

In summary, the control electronics 71 provide the necessary interfacing between the X-Y table 69 and the printed circuit board 11 for movement of the table, for inspection of the printed circuit board, and for compiling and utilizing the information collected.

It will thus be seen that the objects set forth above, those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An optical inspection unit for inspecting an irregular surface of an object such as the solder surface of a substantially flat printed circuit board comprising means supporting the object while exposing its surface to be inspected, a maneuvering base adjacent to the supported object and having a mounting plate facing said surface and spaced therefrom, X-Y maneuvering means associated with said base and said object supporting means and connected to produce successive relative repositioning movements of the plate and the surface upon command, a thick-walled translucent concave dome having a hollow central cavity bounded by a rim, with the cavity being defined by an interior face arching internally away from said inspected surface, the dome being centrally mounted on the mounting plate with its central cavity opening toward and its rim closely juxtaposed to said surface, substantially blocking external illumination from passing between said rim and said surface, external illumination means aimed to direct illumination on the external face of the dome, and inspection portal means formed in the dome each defined by a portal axis intersecting a central region of said surface to be inspected, through which optical inspection of said surface can be made, whereby diffuse illumination of said surface substantially without bright spots, specular reflections or glare is produced within the cavity by attenuation of externally delivered illumination through absorption and internal reflection as it passes through the thick wall of the translucent concave dome, enhancing the precision of optical inspection of said surface performed through said inspection portal means.

2. An optical inspection unit for inspecting an irregular surface of an object such as the soldered surface of a printed circuit board comprising means supporting the object with its surface to be inspected facing downward, a maneuvering base underlying the supported object and having a maneuverable mounting plate facing said surface and spaced therebelow, positionable in its own plane relative to the surface, X-Y maneuvering means incorporated in said base and connected to produce each successive desired repositioning movement of the plate relative to the surface upon command, a thick-walled translucent concave dome having a hollow central cavity bounded by a rim, with the cavity being defined by an interior face arching internally away from said inspected surface, the dome being centrally mounted on the maneuverable mounting plate with its central cavity opening upward and its rim closely juxtaposed to said surface, substantially blocking external illumination from passing between said rim and said surface, external illumination means aimed to direct illumination on the external face of the dome, and inspection portal means formed in the dome through which optical inspection of said surface can be made, each such portal means being defined by a portal axis intersection a central region of said surface to be inspected, whereby diffuse illumination of said surface substantially without bright spots, specular reflections or glare is produced within the cavity by attenuation of externally delivered illumination through absorption and internal reflection as it passes through the thick wall of the translucent concave dome, enhancing the precision of optical inspection of said surface performed through said inspection portal means.

3. The optical inspection unit for inspecting the surface of an object defined in claim 2, wherein the concave dome is formed as a minor sector of a sphere.

4. The optical inspection unit defined in claim 3, wherein the wall thickness of the translucent dome is between about 20% and about 50% of the dome's external radius.

5. An optical inspection unit for inspecting the surface of an object such as the soldered surface of a printed circuit board comprising
   means supporting the object while exposing its surface to be inspected,
   a maneuvering base adjacent to the supported object and having a mounting plate facing said surface and spaced therefrom,
   X-Y maneuvering means associated with said base and said object supporting means and connected to produce successive relative repositioning movements of the plate and the surface upon command,
   a thick-walled translucent concave dome having a hollow central cavity bounded by a rim, and centrally mounted on the mounting plate with its central cavity opening toward and its rim juxtaposed to said surface,
   external illumination means aimed to direct illumination on the external face of the dome,
   and inspection portal means formed in the dome each defined by a portal axis intersecting a central region of said surface to be inspected, through which optical inspection of said surface can be made,
   wherein the rim of the concave dome is spaced away from said surface, and further including a flexible translucent skirt extending from the dome rim into flexing contact with said surface, blocking direct penetration of illumination between the dome and the juxtaposed surface,
whereby diffuse illumination of said surface substantially without bright spots, specular reflections or glare is produced within the cavity by attenuation of externally delivered illumination through absorption and internal reflection as it passes through the thick wall of the translucent concave dome, enhancing the precision of optical inspection of said surface performed through said inspection portal means.

6. The optical inspection unit defined in claim 5, wherein both dome and skirt are formed of white translucent material.

7. The optical inspection unit defined in claim 5, wherein the flexible translucent skirt is formed of a large plurality of resilient, translucent bristles having their ends embedded in the rim of the dome.

8. The optical inspection unit defined in claim 7, wherein the thick-walled translucent dome is made of polyethylene, and the resilient translucent bristles are made of nylon.

9. An optical inspection unit for inspecting the surface of an object such as the soldered surface of a printed circuit board comprising
   means supporting the object while exposing its surface to be inspected,
   a maneuvering base adjacent to the supported object and having a mounting plate facing said surface and spaced therefrom,
   X-Y maneuvering means associated with said base and said object supporting means and connected to produce successive relative repositioning movements of the plate and the surface upon command,
   a thick-walled translucent concave dome having a hollow central cavity bounded by a rim, and centrally mounted on the mounting plate with its central cavity opening toward and its rim juxtaposed to said surface,
   external illumination means aimed to direct illumination on the external face of the dome,
   and inspection portal means formed in the dome defined by a portal axis intersecting a central region of said surface to be inspected, through which optical inspection of said surface can be made,
further incorporating a light baffle assembly aligned along each portal axis adjacent to its inspection portal means, including
   a hollow baffle tube having a baffle axis substantially coinciding with said portal axis,
   and a plurality of pairs of baffle rings successively positioned inside the baffle tube,
   each ring having a generally triangular cross-section defined by an outer rim wall facing the inner surface of the baffle tube, a radial base wall facing the adjacent ring of the pair, and a conical chamfered wall facing the hollow interior of the tube,
   and each pair of rings including a light-colored translucent ring whose conical chamfered wall faces the baffle axis toward the portal opening into the central cavity of the concave
   and a dark-colored opaque ring whose conical chamfered wall faces the baffle axis away from said portal,
whereby the size of the portal viewed from inside the dome is minimized, and stray light entering the baffle tube and reflected by a light-colored ring is absorbed by a dark-colored ring, and whereby diffuse illumination of said surface substantially without bright spots, specular reflections or glare is produced within the cavity by attenuation of externally delivered illumination through absorption and internal reflection as it passes through the thick wall of the translucent concave dome, enhancing the precision of optical inspection of said surface performed through said inspection portal means.

10. The optical inspection unit defined in claim 9, wherein the baffle tube and the light-colored rings are formed of white translucent material and the dark-colored opaque rings are formed of black material.

11. The optical inspection unit defined in claim 9, further including a video camera connected to view the interior cavity of the dome along the axis of a baffle tube generally coinciding with the portal axis.

12. The optical inspection unit defined in claim 11, wherein the video camera and associated baffle tube are anchored together and movable relative to the dome, providing angular adjustment of the baffle axis relative to the portal axis for adjustable selection of the interior zone of the dome's cavity to be imaged by the video camera.

* * * * *